United States Patent [19]

Pitterna et al.

[11] Patent Number: 5,606,057

[45] Date of Patent: Feb. 25, 1997

[54] PROCESS FOR THE PREPARATION OF 6-ALKYL-4-(PYRIDIN-3-YL-METHYLENEAMINO)-4,5-DIHYDRO-1,2,4-TRIAZIN-3(2H)-ONE

[75] Inventors: Thomas Pitterna, Basel; Urs Siegrist, Eiken; Henry Szczepanski, Wallbach, all of Switzerland

[73] Assignee: Ciba-Geigy Corporation, Ardsley, N.Y.

[21] Appl. No.: 194,183

[22] Filed: Feb. 9, 1994

[30] Foreign Application Priority Data

Mar. 2, 1993 [GB] United Kingdom ............ 9304178

[51] Int. Cl.⁶ ............................................. C07D 253/06
[52] U.S. Cl. ............................................. 544/182
[58] Field of Search ............................................. 544/182

[56] References Cited

U.S. PATENT DOCUMENTS

| | | | |
|---|---|---|---|
| 2,798,077 | 7/1957 | Schläpfer et al. | 260/296 |
| 2,945,862 | 7/1960 | Mignomac et al. | 260/297 |
| 3,274,206 | 9/1966 | Wilbert et al. | 260/297 |
| 5,179,094 | 1/1993 | Kristiansen et al. | 544/182 |

FOREIGN PATENT DOCUMENTS

| | | |
|---|---|---|
| 0314615 | 5/1989 | European Pat. Off. . |
| 0391849 | 10/1990 | European Pat. Off. . |
| 0433218 | 6/1991 | European Pat. Off. . |
| 43044 | 1/1966 | Germany . |
| 43047 | 2/1966 | Germany . |
| 9202507 | 2/1992 | WIPO . |

OTHER PUBLICATIONS

Plieninger et al, Chem Ber., 88, pp. 1956–1961 (1955).
Mathes et al., Chemiker–Zeitung, vol. 80, p. 475 (1956).
Mathes et al., Chemiker–Zeitung, vol. 82, p. 647 (1958).
Felder et al., Gazzetta Chimica Italiana, LXXXVI, pp. 386–391 (1956).
Derwent Abst. 92–092944/12 (corresponding to JP 4,036, 250) May 30, 1990.

Primary Examiner—John M. Ford
Attorney, Agent, or Firm—Marla J. Mathias

[57] ABSTRACT

A process for the preparation of 6-alkyl-4-(pyridin-3-yl-methyleneamino)-4,5-dihydro-1,2,4-triazin-3(2H)-one by the reaction of 4-amino-6-alkyl-3-oxo-2,3,4,5-tetrahydro-1, 2,4-triazine with 3-cyanopyridine wherein the reaction is carried out under catalytic hydrogenation conditions in the presence of a Raney-nickel catalyst in an aqueous alcoholic medium, at a temperature between 0° and 70° C., at a pH of between 2 and 7, and in the presence of and a $C_1$–$C_6$-carboxylic acid or a $C_1$–$C_6$-carboxylic acid alkali metal salt or both, whereby the hydrogen pressure is between 0.1 and 10 bar.

12 Claims, No Drawings

PROCESS FOR THE PREPARATION OF 6-ALKYL-4-(PYRIDIN-3-YL-METHYLENEAMINO)-4,5-DIHYDRO-1,2,4-TRIAZIN-3(2H)-ONE

The present invention relates to a process for the preparation of 6-alkyl-4-(pyridin-3-yl-methyleneamino)-4,5-dihydro-1,2,4-triazin-3(2H)-one by reaction between an aminotriazinone and 3-cyanopyridine under catalytic hydrogenation conditions.

6-Methyl-4-(pyridin-3-yl-methyleneamino)-4,5-dihydro-1,2,4-triazin-3(2H)-one is a known insecticide and is also a useful intermediate in the synthesis of insecticidally active compounds, as described for example in published European patent application EP-A-0 314 615.

In EP-A-0 314 615 there is described a process for the preparation of 6-alkyl-4-(pyridin-3-yl-methyleneamino)-4,5-dihydro-1,2,4-triazin-3(2H)-one by the reaction between pyridine-3-aldehyde and 4-amino-6-alkyl-3-oxo-2,3,4,5-tetrahydro-1,2,4-triazine in the presence of catalytic amounts of a strong acid. The disadvantages of this process are the difficult handling and high price of the pyridin-3-aldehyde.

Published PCT application WO 92/02507 describes a two-step process for the synthesis of imines by the hydrogenation of pyridinecarbonitriles with amines in the presence of a rhodium-loaded catalyst. There is no mention of hydrazone formation. Addition of a strong acid, for example HCl, is advocated in order to drive the equilibrium towards reaction-completion. This has the disadvantage of causing ammonium chloride formation which, combined with the acidic environment, can lead to fast corrosion and deterioration of the reaction vessel. Another disadvantage is that the use of rhodium in industrial production processes is extremely expensive.

H. Plieninger and G. Werst report the preparation of aldehyde derivatives from nitriles in Chem. Ber. 88, p. 1956 to 1961 (1955). Semicarbacides are used as starting materials, and the reaction conditions include relatively large amounts of Raney-nickel catalyst and high hydrogen pressure. Furthermore poor yields are achieved. In contrast to Plieninger et al. the present invention uses a cyclic carbacide as starting material, smaller amounts of catalyst and lower hydrogen pressure.

There is a need for a more economical and ecologically acceptable process. The disadvantages of the known processes include low selectivity, poor yields and corrosion of the production vessels.

Surprisingly it has now been found that 6-alkyl-4-(pyridin-3-yl-methyleneamino)-4,5-dihydro-1,2,4-triazin-3(2H)-one can be prepared directly in a one-pot reaction between an aminotriazinone, namely 4-amino-6-alkyl-3-oxo-2,3,4,5-tetrahydro-1,2,4-triazine, and 3-cyanopyridine in high yield, high selectivity and under mild conditions. The handling difficulties encountered with pyridin-3-aldehyde are avoided since there is no isolation of intermediates, and the use of expensive rhodium is avoided. It is also surprising that the conditions according to the present invention are so selective that neither the starting compounds nor the end-products are hydrogenated further.

The reaction selectivity of the present invention is particularly surprising in view of the process described in U.S. Pat. No. 2,798,077. In U.S. Pat. No. 2,798,077 for example there is described a process in which 3-cyanopyridine is hydrogenated in the presence of methylamine and Raney-nickel to give methyl-(β-picolyl)-amine and β-picolylamine.

The object of the invention is a process for the preparation of 6-alkyl-4-(pyridin-3-yl-methyleneamino)-4,5-dihydro-1,2,4-triazin-3(2H)-one of the formula I

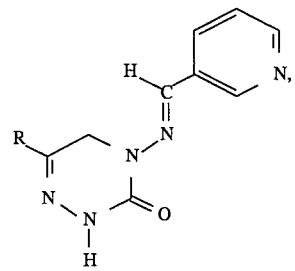

where R is methyl, ethyl, propyl, cyclopropyl, or n- or t-butyl, by the reaction of an aminotriazinone, of the formula II

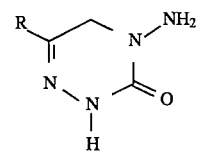

or of the corresponding hydrogen chloride of formula IIa

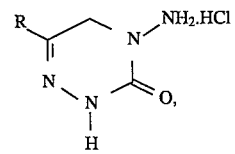

in which R is as defined in formula I, with 3-cyanopyridine of the formula III

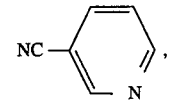

wherein the reaction is carried out under catalytic hydrogenation conditions in the presence of a Raney-nickel catalyst in an aqueous alcoholic medium, at a temperature between 0° and 70° C., at a pH of between 2 and 7, and in the presence of a $C_1$–$C_6$ carboxylic acid, whereby the hydrogen pressure is between 0.1 and 10 bar.

R is preferably methyl or ethyl.

Suitable $C_1$–$C_6$ carboxylic acids are for example formic acid, acetic acid, propanoic acid, butyric acid, valeric acid or caproic acid, preferably acetic acid. It is also possible to use from begin of the reaction the alkali salts of said carboxylic acids, preferred are the sodium salts.

During the reaction ammonium salts of the carboxylic acids are formed, acting as a buffer system.

The reaction is conducted preferably at between 10° and 50° C., more preferably between 10° and 30° C., and most preferably at room temperature.

The hydrogen pressure is preferably between 0.1 and 5 bar, and more preferably between 0.1 and 1 bar.

The solvent medium can comprise water, an alcohol, e.g. methanol, ethanol, or n- or i-propanol, or a mixture of these alcohols in water. A suitable alcohol content is between 50 and 90%, preferably 70 to 90%. Particularly preferred is an 80:20 methanol:water medium.

To complete the reaction of the aminotriazinone, a 10 to 40% excess cyanopyridine with respect to the aminotriazinone is suitable, preferably a 20 to 40% excess and most preferably a 20 to 30% excess.

The catalyst concentration is preferably between 5 and 7 wt-% with respect to the cyanopyridine.

The pH buffer can additionally comprise a carboxylic acid, e.g. formic, acetic, propanoic or butyric acid, and acetates of alkaline or alkaline earth metals, and ammonia. Oxides such as magnesium oxide, calcium oxide or carbon dioxide dissolved in water can also be used. An acetic acid/sodium acetate buffer is preferred.

The pH is preferably between 3,5 and 6.

The preferred concentration of compounds of formula II or IIa and III in aqueous alcohol is between 20 and 50 weight %, preferably 30 to 50 wt-%.

The starting compounds of the present invention are available commercially or can be synthesised by known methods. A process for the preparation of aminotriazine derivatives including compounds of the formula II is described, for example, in published European application EP-A-0 433 218.

An in situ preparation of starting compounds II or IIa is preferred.

In the practise of the present invention, compounds of formula I, for example 6-methyl-4-(pyridin-3-yl-methyleneamino)-4,5-dihydro-1,2,4-triazin-3(2H)-one, are prepared by the combination of an aminotriazinone of formula II, or its hydrogen chloride equivalent of formula IIa, with 3-cyanopyridine in a pressure-resistant vessel, e.g. an autoclave, in the presence of an aqueous alcoholic medium, a pH buffer, and a Raney-nickel catalyst under a hydrogen atmosphere at room temperature. The reaction time, determined by the hydrogen uptake, is typically between 3 and 6 hours. After the catalytic hydrogenation is complete, the reaction mixture is filtered, optionally after warming, the Raney-nickel separated, and the crystalline title compound isolated by known methods.

The advantages of the process of the present invention are as follows:

i) high reaction selectivity is achieved, leading to a purer end product, ii) high yield is achieved, e.g. above 98% under optimised conditions, iii) the handling of aldehyde is avoided, iv) a low hydrogen pressure is used, v) there is negligible vessel corrosion, vi) very high reactant turnover is achieved, vii) a cheap catalyst is used which suffers low catalytic corrosion, viii) there is a very low metal contamination of the end product, and ix) the process is carried out in a single reaction vessel.

The following Examples demonstrate the process of the invention.

EXAMPLE 1

Preparation of
6-Methyl-4-(pyridin-3-yl-methyleneamino)-
4,5-dihydro-1,2,4-triazin-3(2H)-one from
Aminotriazinone An aliquot of 400 g of an aqueous suspension of the aminotriazinone 4-amino-6-methyl-3-oxo-2,3,4,5-tetrahydro-1,2,4-triazine containing 0.5 mol aminotriazinone, is added to an autoclave with 170 g methanol and 40 g water. 65 g 3-cyanopyridine and 30 g acetic acid are added, after which 7.6 g moist Raney-nickel (nickel content ~60%) are added and hydrogenation carried out at room temperature at a constant 1 bar hydrogen pressure. After hydrogen uptake is completed, the reaction mixture is quenched with 480 g methanol and 100 g water. The catalyst is separated by filtration after warming to 70° C. The reaction vessel is rinsed first with 150 g methanol and then 150 g water. 300 g water are added to the cooled filtrate and the methanol is distilled off by means of a rotation evaporator. The precipitated title compound is filtered off and washed with water. After drying there are obtained 102.1 g title compound (mp 230°–234° C.) with a 98.3% purity (HPLC) and a 92.5% yield.

EXAMPLE 2

Preparation of
6-Methyl-4-(pyridin-3-yl-methyleneamino)-
4,5-dihydro-1,2,4-triazin-3(2H)-one from
Aminotriazinone Hydrochloride 9.5 g 3-cyanopyridine and 11.6 g aminotriazinone-hydrochloride are mixed in an autoclave at room temperature with a methanol solution consisting of 40.6 g methanol and 9.8 g water. 6.3 g anhydrous sodium acetate are added to the suspension. After brief stirring the pH is about 5. 1.1 g aqueous Raney-nickel (nickel content ~60%) are added to the suspension and the hydrogenation is started by filling the autoclave with hydrogen to a pressure of 1 bar. The reaction is complete after 4 hours at room temperature, after which 79 g methanol and 20 g water are added to the reaction mixture. The reaction mixture is heated to 70° C. and the catalyst is separated by filtration. 70 ml water are added to the cooled filtrate and the methanol is distilled off by means of a rotation evaporator. The precipitated title compound is filtered off and washed with water. After drying there are obtained 15.3 g title compound (mp 230°–234° C.) with a 98.6% purity as determined by HPLC and a 98.6% yield. The nickel lost from the catalyst is 8.6 mg and corresponds to about 1.3% of the total nickel content.

What is claimed is:

1. A process for the preparation of 6-alkyl-4-(pyridin-3-yl-methyleneamino)-4,5-dihydro-1,2,4-triazin-3(2H)-one of the formula I

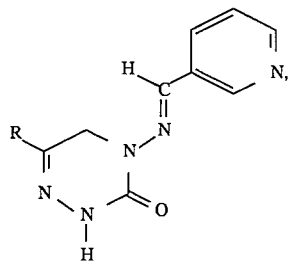

where R is methyl, ethyl, propyl, cyclopropyl, or n- or t-butyl, by the reaction of an aminotriazinone, 4-amino-6-alkyl-3-oxo-2,3,4,5-tetrahydro-1,2,4-triazine, of the formula II

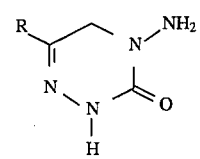

or of the corresponding hydrogen chloride of formula IIa

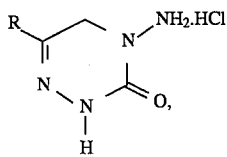

in which R is as defined in formula I, with 3-cyanopyridine of the formula III

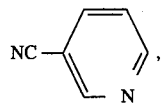

wherein the reaction is carried out under catalytic hydrogenation conditions in the presence of a Raney-nickel catalyst in an aqueous or aqueous alcoholic medium, at a temperature between 0° and 70° C., at a pH of between 2 and 7, and in the presence of a $C_1$–$C_6$-carboxylic acid or $C_1$–$C_6$-carboxylic acid alkali metal salt or both, whereby the hydrogen pressure is between 0.1 and 10 bar.

2. A process according to claim 1, wherein the $C_1$–$C_6$-carboxylic acid is acetic acid and the $C_1$–$C_6$ carboxylic acid alkali metal salt is sodium acetate.

3. A process according to claim 1, wherein R is methyl or ethyl.

4. A process according to claim 1, wherein the reaction is conducted at between 10° and 50° C.

5. A process according to claim 1, wherein the hydrogen pressure is between 0.1 and 5 bar.

6. A process according to claim 1, wherein the solvent medium comprises a water/alcohol mixture.

7. A process according to claim 6, wherein the solvent medium is a 80:20 methanol:water mixture.

8. A process according to claim 1, wherein a 10 to 40% excess of 3-cyanopyridine with respect to the aminotriazinone is used.

9. A process according to claim 1, wherein the catalyst concentration is between 5 and 7 wt-% with respect to the cyanopyridine.

10. A process according to claim 1, wherein the pH buffer is an acetic acid/sodium acetate mixture.

11. A process according to claim 1, wherein the pH is between 3,5 and 6.

12. A process according to claim 1, wherein the concentration of compounds of formula II or IIa and III in the aqueous or aqueous alcohol medium is between 20 and 50 weight %.

* * * * *